United States Patent
Millay et al.

(10) Patent No.: US 7,166,077 B2
(45) Date of Patent: Jan. 23, 2007

(54) CUFF FOR MEASUREMENT OF BLOOD PRESSURE

(75) Inventors: Jack Millay, Beaverton, OR (US); Paul Patterson, Beaverton, OR (US)

(73) Assignee: Pharma-Smart, LLC, Rochester, NY (US)

( * ) Notice: Subject to any disclaimer, the term of this patent is extended or adjusted under 35 U.S.C. 154(b) by 331 days.

(21) Appl. No.: 10/771,251

(22) Filed: Feb. 3, 2004

(65) Prior Publication Data

US 2005/0182331 A1   Aug. 18, 2005

(51) Int. Cl.
*A61B 5/00* (2006.01)
(52) U.S. Cl. .................. 600/499; 600/485; 600/490
(58) Field of Classification Search ................ 600/485, 600/490–500
See application file for complete search history.

(56) References Cited

U.S. PATENT DOCUMENTS

| | | | |
|---|---|---|---|
| 2,678,040 A | | 5/1954 | Poole et al. |
| 3,760,795 A | | 9/1973 | Adelhed |
| 3,812,844 A | * | 5/1974 | Sokol ........................ 600/499 |
| 3,905,353 A | * | 9/1975 | Lichowsky ................ 600/490 |
| 3,906,937 A | * | 9/1975 | Aronson ................... 600/493 |
| 4,007,734 A | * | 2/1977 | Peters ....................... 600/490 |
| 4,920,971 A | * | 5/1990 | Blessinger ................ 600/492 |
| 5,069,219 A | * | 12/1991 | Knoblich .................. 600/492 |
| 5,660,182 A | * | 8/1997 | Kuroshaki et al. ......... 600/499 |
| 5,680,869 A | * | 10/1997 | Ogura ....................... 600/485 |
| 6,213,953 B1 | | 4/2001 | Reeves |
| 6,290,653 B1 | | 9/2001 | Che et al. |
| 6,551,249 B2 | * | 4/2003 | Ashida et al. ............ 600/499 |
| 6,988,992 B2 | * | 1/2006 | Just et al. ................. 600/499 |

\* cited by examiner

*Primary Examiner*—Robert L. Nasser
*Assistant Examiner*—Karen Toth
(74) *Attorney, Agent, or Firm*—Neal L. Slifkin; Robert C. Brown (57) ABSTRACT

A blood pressure cuff including an inflatable bladder disposed between an elastic, resilient inner layer of material and at least one outer layer of material. The bladder is secured to these layers along the elongate ends but not along the elongate edges. The bladder is not laterally constrained during inflation. The cuff is formed into a cylindrical shape having a fixed outer diameter and includes a backing layer and apparatus for securing the bladder to a layer of the cuff to hold the bladder in place during donning of the cuff. Because the bladder is not constrained along its contact-width edges, the shape of the bladder automatically adjusts to provide a longer contact surface for larger arms and a shorter contact surface for smaller arms. The cuff is especially suited for use as a closed cuff in an automated blood pressure measurement machine or in stand-alone measurement use.

14 Claims, 6 Drawing Sheets

CUFF FOR MEASUREMENT OF BLOOD PRESSURE

TECHNICAL FIELD

The present invention relates to devices for measuring systolic, mean, and diastolic blood pressures in animals; more particularly, to inflatable devices for measuring such blood pressures in humans; and most particularly, to an improved inflatable cuff for obtaining more accurate blood pressure measurements over a greater range of arm sizes.

BACKGROUND OF THE INVENTION

The measurement of systolic, mean, and diastolic blood pressures, referred to herein collectively as "blood pressure," is an important and well-known diagnostic procedure in animal medicine, and especially in human medicine. Blood pressure may be measured either directly, by insertion of a pressure-measuring catheter into an artery, or indirectly (inferentially), usually by means of an inflatable cuff. In using a cuff, the operative principle is that pneumatically inflating the cuff compresses an underlying artery in the subject, and the respective pressures are determined as air pressure is gradually released from the cuff.

In design, known cuffs are either open or closed. An open cuff is a flat device which is wrapped around the subject's extremity. A closed cuff is a generally cylindrical device through which a subject's extremity is inserted.

In operation, a typical cuff is applied to encircle an upper arm, thigh, or in some cases, a wrist or forearm. The cuff is then inflated to an indicated cuff air pressure at which the flow of blood through the underlying artery is stopped, such air pressure being greater than the subject's systolic pressure. Pressure within the cuff is then gradually reduced. When blood flow through the artery resumes, the cuff pressure corresponds to the subject's systolic pressure. When pressure in the cuff drops below the subject's diastolic pressure, blood flows in the artery through the complete cardiac cycle. Optionally, mean blood pressure may also be determined.

These flow phenomena can be determined in any of several ways: for example, a) by listening via a stethoscope to the sounds emanating from the artery downstream of the cuff; b) by observing the relatively small changes in pressure in the cuff caused by the encircled artery's opening and closing during the cardiac cycle; or, c) by using a Doppler flowmeter to measure flow rates. Each of these methods is well known in the art.

There are several potential sources of error in determining blood pressure using a prior art inflatable open cuff. An important consideration is that the dimensions of the cuff be selected to fit the subject to be tested. The contact dimension of a cuff in a direction along a subject's arm is referred to herein as the cuff contact width, and the contact dimension circumferential of the relaxed arm is the circumference, or contact length. Preferably, the contact width of the cuff is about 40% of the arm circumference, and the contact length of the inflatable part of the cuff is at least 70% of the arm circumference. If the total contact area of the cuff is too narrow, blood pressure is over-estimated; if the area is too wide, pressure is under-estimated.

In common medical practice, either a wrap-around cuff of proper dimensions or a closed (cylindrical) cuff of fixed dimensions is used. In stand-alone uses today (stand-alone being defined as not being part of an automated blood pressure machine), a "wrap-around" cuff is typically employed. Such a cuff comprises an elongate flat fabric pocket formed of non-elastic material into which a distensible bladder is inserted for pneumatic inflation. The cuff is wrapped snugly around the subject's extremity, such as an arm or leg, and is then secured in place, for example, by Velcro attachments. (As used hereinbelow, the term "arm" should be taken generally to mean any of the various anatomical extremities or appendages in which blood pressure may be measured with a cuff.) Typically, the bladder is not attached to the fabric of the cuff and thus is free to conform to each subject's arm in both contact width and contact length.

Because proper contact length is important for accurate blood pressure measurement, the circumference of a subject's arm should be determined before attempting blood pressure measurement with an open cuff. In good medical practice, the circumference of the subject's arm determines the size cuff to be used. For adult humans, a choice of open cuffs may include three sizes standard in the art: Small Adult, Normal Adult, and Large Adult. Each cuff is sized for an arm circumference in the middle of a range which overlaps the range of an adjacent cuff. For example, a Normal Adult cuff may be specified for use on arm circumferences of 25–35 cm, and a Large Adult cuff may be specified for circumferences of 33–47 cm. Either cuff may be used on a 34 cm arm, but neither cuff is optimal because the contact width of the cuff is optimized for the middle of each range. Blood pressure measurements of a given subject using the two different cuffs may differ by several mmHg. Of course, a greater number of different cuffs, each having a narrower range of arm sizes, would lessen this error but would require a large and unwieldy inventory of open cuffs at each measurement site.

Unfortunately, it is common in stand-alone use to ignore the benefits of sizing the cuff to the subject and to simply use one cuff for all subjects, with concomitant sacrifices in accuracy. What is needed in the stand-alone art is a single cuff that can provide accurate blood pressure measurement over a very wide range of arm sizes.

Closed cuffs also present a serious problem in use. A principal prior art use for closed cuffs is in automated measurement machines. Such machines are intended to make correct measurements on the entire population of human users using a single cuff. Because the cuff is closed, the nominal outer and deflated inner diameters are fixed at manufacture to accommodate the largest arm intended for measurement, and the inflation means is attached to the fabric of the pocket. Therefore, the cuff must expand radially inwards first to occupy the slack space necessary to permit insertion of an arm into the cuff, and then further to properly compress the inserted arm.

The main source of error in using an oversize closed cuff arises from severe puckering of the cuff material. In the prior art, an inflation chamber is formed by heat sealing and then stitching or gluing together two air-impermeable layers of non-distensible, non-elastic material along all four edges thereof. An outer material shell and seam tape are also stitched into the cuff, making the cuff relatively stiff and non-compliant. As the chamber is inflated, the inner layer is forced into relatively large radial puckers or wrinkles, and especially so if the subject's arm is relatively small in circumference. These puckers constitute breaks in the encircling pressure and can lead to outright failure of the measurement when a pucker is formed over the brachial artery being tested. Further, chamber pressure significantly higher than systolic may be required to close the puckers and the underlying artery, thus giving a falsely high measurement of systolic pressure. Further, because the chamber layers are constrained along all four edges, the inflation chamber cannot readily collapse transversely to form a desirable oval cross-sectional shape.

What is needed is an improved blood pressure closed cuff that can provide accurate measurement in an automated blood pressure machine over the full range of arm sizes of potential human users.

It is a principal object of the present invention to make accurate measurements of blood pressure over a wide range of human arm sizes using a single cuff.

It is a further object of the invention to make such measurements via an automated blood pressure machine.

It is a still further object of the invention to make such measurements in stand-alone use.

SUMMARY OF THE INVENTION

Briefly described, a closed blood pressure cuff in accordance with the invention includes an elongate inflatable bladder disposed between an elastic, resilient inner layer of material and at least one outer layer of material. The bladder is secured to these layers as by stitching along the elongate ends but not along the elongate edges as in the prior art. Thus the bladder is not laterally constrained during inflation and can more readily conform to a subject's limb. The cuff is formed, as by stitching or gluing together of the bladder ends together with the inner and outer layer ends, into a cylindrical shape having a fixed outer diameter that is selected to accommodate an upper limit of arm circumference within the cuff. In an alternate embodiment, the bladder may be formed as a continuous ring-shaped element analogous to the inner tube of an automotive tire.

For machine use, the cuff preferably includes a relatively stiff backing layer outboard of the bladder for supporting and constraining the bladder to maintain cuff integrity when deflated. For stand-alone use, the stiff backing layer preferably is omitted so that the cuff may be conveniently folded flat for storage. In both configurations, the outer layer is non-elastic and therefore provides an invariant radial platform against outward pressure from the bladder during inflation.

Preferably, the bladder is attached to the outer layer to prevent the bladder from being rolled out of the cuff during donning of the cuff by a subject. Such attachment may include, for example, an adhesive stripe, a plurality of tabs, or a flexible longitudinal fin integral to the outer surface of the bladder and secured to the outer layer of material. Because the bladder is not constrained along its contact-width edges, the cross-sectional shape of the bladder is thus automatically adjusted by inflation to provide a longer contact surface for larger circumference arms and a shorter contact surface for smaller circumference arms, making the cuff useful over a much wider range of arm sizes than can be accommodated by any single prior art cuff.

A cuff in accordance with the invention is well suited for use in either an automated blood pressure measurement machine or stand-alone measurement.

BRIEF DESCRIPTION OF THE DRAWINGS

The present invention will now be described, by way of example, with reference to the accompanying drawings, in which.

DESCRIPTION OF THE PREFERRED EMBODIMENTS

Referring to FIGS. 1 through 4, a user-interface portion of an automated blood pressure measurement machine 10 includes a generally cylindrical closed inflatable cuff 12 disposed within a rigid cylindrical housing 14 being supported by a brace 16. Cuff 12 is connected pneumatically to an actuation and control portion (not shown) of the machine whereby pressurized air is supplied to and withdrawn from the cuff in known fashion. Cuff 12 selectively compresses an artery in a user's arm 18, after insertion through the cuff to position the cuff at the user's bicep, to determine inferentially the blood pressures of the cuff user or subject. Cuff 12 may be a prior art closed cuff 12 (FIG. 3) or an improved closed cuff 12',12" (FIGS. 4 and 11) as described hereinbelow.

A typical prior art closed cuff 12 is formed from three layers of flat fabric cut from fabric material stock and joined as by stitching 20 and sealing along the longitudinal 22 and transverse 24 edges. The stitched sub-assembly is then rolled around a transverse axis into a closed form approximating a cylinder and the ends are joined 26 as by gluing or stitching.

Figure 1:
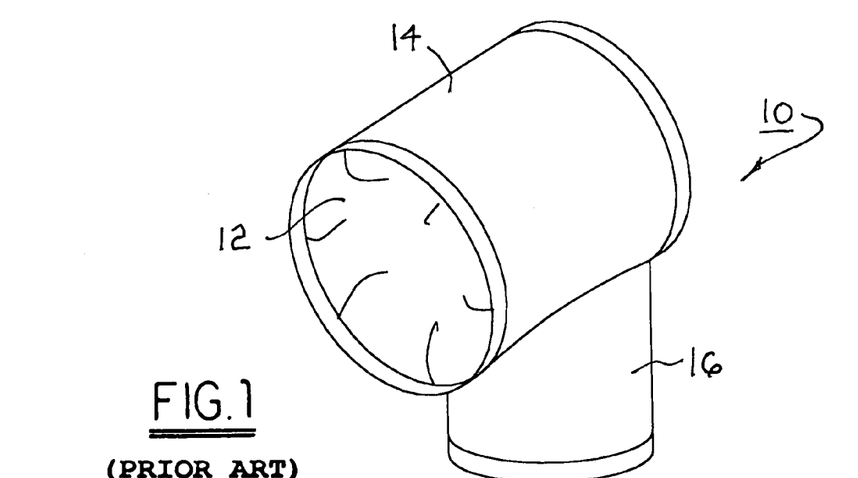
FIG. 1 is an isometric view of a prior art closed cuff in an automated blood pressure measurement machine.
Figure 2:
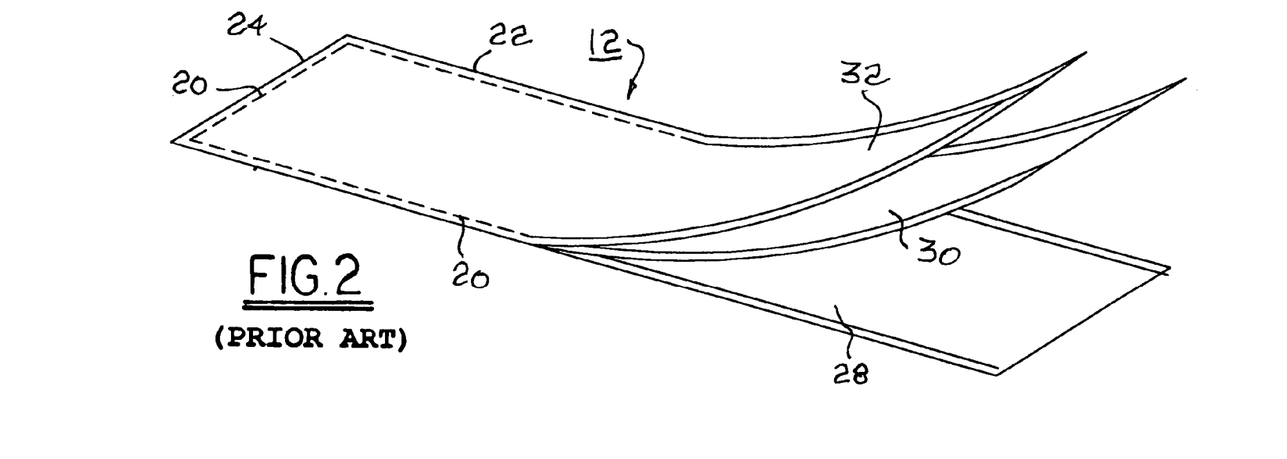
FIG. 2 is an isometric view showing the arrangement of layers in a prior art cuff.
Figure 3:
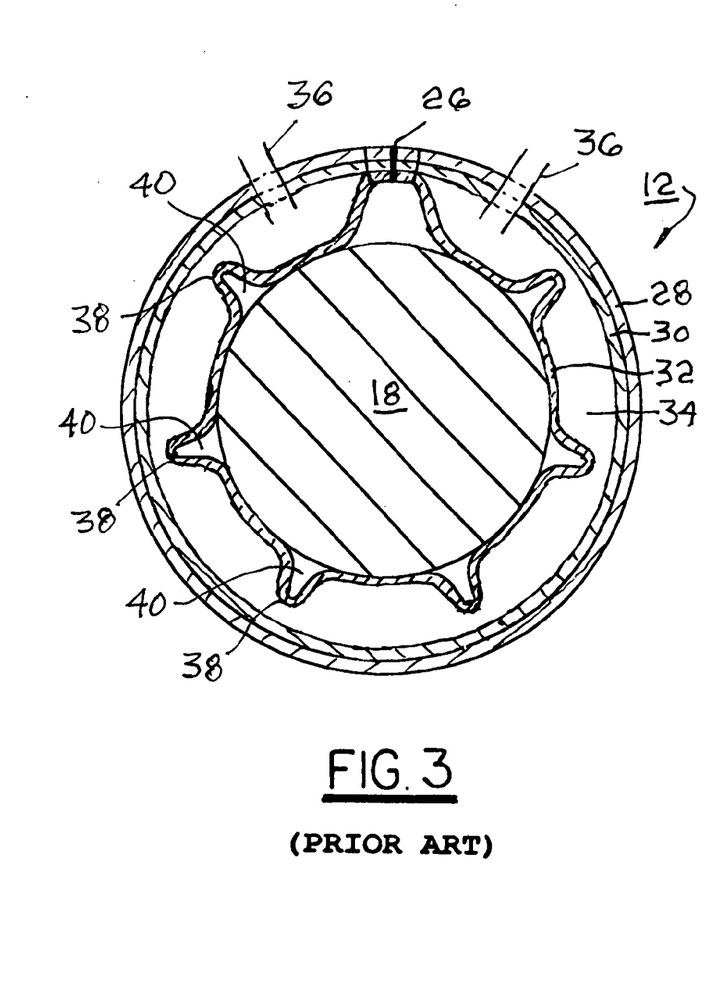
FIG. 3 is a cross-sectional view of an inflated prior art closed cuff.

The outer fabric layer 28 is formed typically of a heavy gauge non-distensible material such as woven nylon shell. The intermediate and inner fabric layers 30,32 are formed also of non-distensible material such as nylon shell but are additionally treated to make them substantially leak-proof against air, the space therebetween defining a pneumatic pressure chamber 34. Chamber 34 is connectable to the actuation and control portion of the machine via one or more air hoses 36 extending through layers 28,30. Because layers 30,32 are formed and joined together as planar elements, as shown in FIG. 2, they exhibit transverse puckers or wrinkles 38 when the planar sub-assembly is rolled into a closed cuff, which wrinkles are exacerbated in at least inner layer 32 after inflation of the cuff, as shown in FIG. 3. Wrinkles 38 define voids 40 which represent areas of non-contact of cuff 12 with the subject's arm 18. As already noted, such areas can seriously compromise the accuracy of blood pressure measurement. It is an important feature of an improved cuff 12' in accordance with the invention to minimize the size of such wrinkles and voids, through novel configuration of the cuff and selection of materials.

Figure 4:
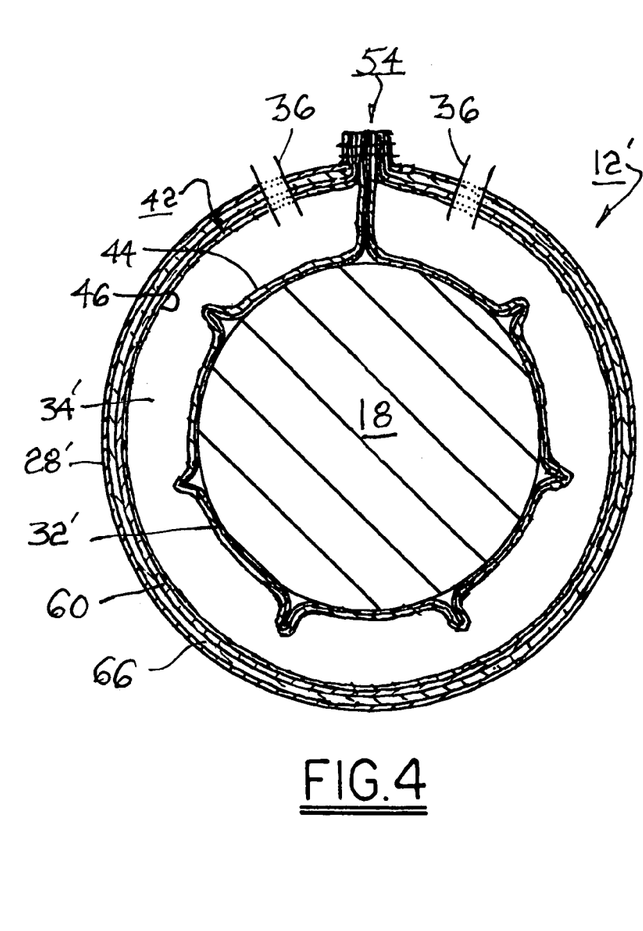
FIG. 4 is a cross-sectional view of a first embodiment of an improved closed cuff in accordance with the invention.
Figure 5:
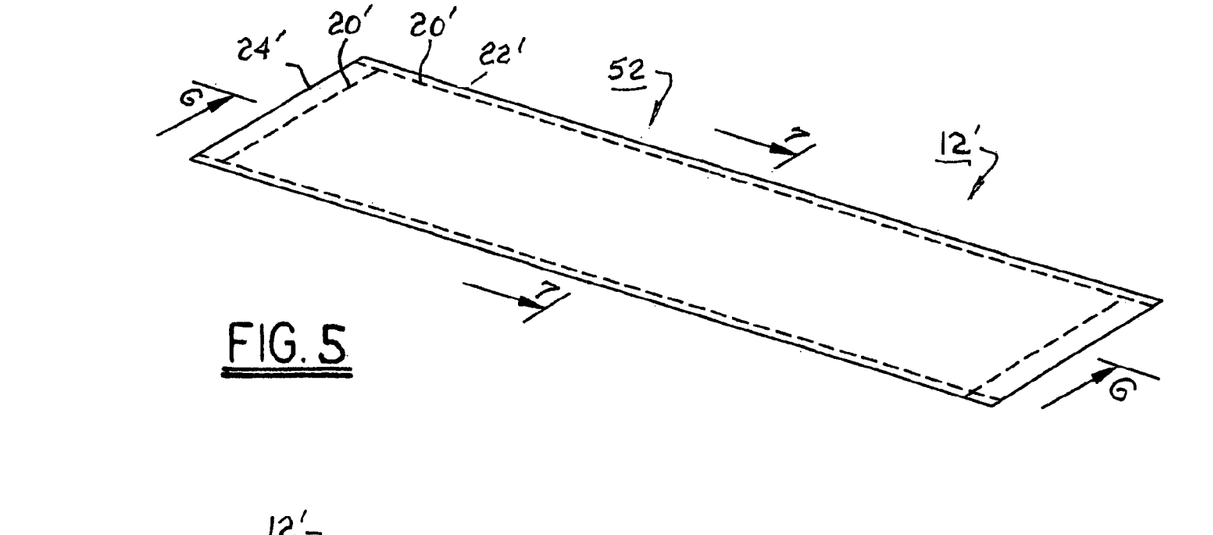
FIG. 5 is an isometric view showing assembly of the improved closed cuff embodiment shown in FIG. 4.

Referring to FIGS. 4 through 10, an improved inflatable closed cuff 12' in accordance with the invention includes an outer layer 28' and an inner layer 32', which layers are joined along their longitudinal and transverse edges 22',24' as by stitching 20', as shown in sub-assembly 52 in FIG. 5, in construction similar to prior art cuff 12. However, a first distinct difference and improvement upon the prior art is that inner layer 32' is formed of a thin, highly-compliant, elastic material, for example, a spandex fabric, which is not given to forming hard wrinkles; thus, non-contact areas 40 are minimized in volume and lateral extent. A particularly suitable material is a spandex omni-directional warp knit available from Shawmut Mills, West Bridgewater, Mass. 02379 under the trade name Darlexx. In addition to being elastic, this material has the added advantage of having a laminated monolithic film on one surface. Layer 32' is oriented during assembly such that the film is in contact with the bladder. Darlexx is able to prevent transpiration of moisture into contact with the bladder, a benefit in a device which might otherwise be readily contaminated by bodily sweat from the multitude of users a cuff will experience, yet can breathe as the enclosed bladder expands and contracts during use.

Outer layer 28' preferably is formed of either nylon shell or a rollable, heavy gauge plastic sheeting.

Figure 6:
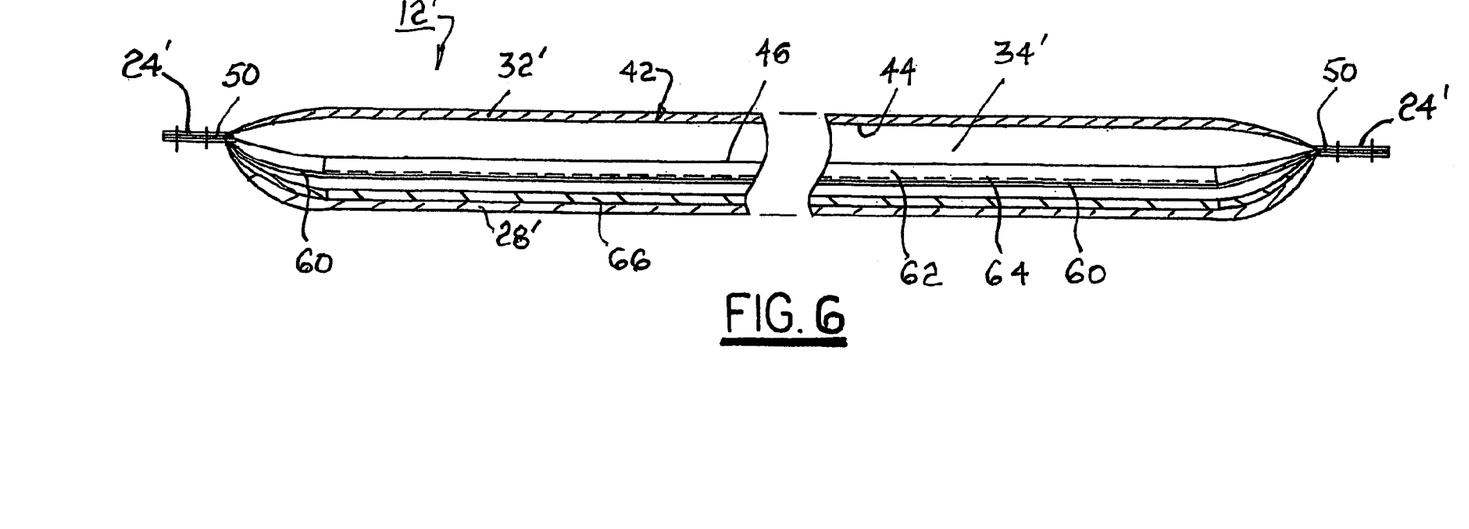
FIG. 6 is a cross-sectional view taken along line 6—6 in FIG. 5.
Figure 7:
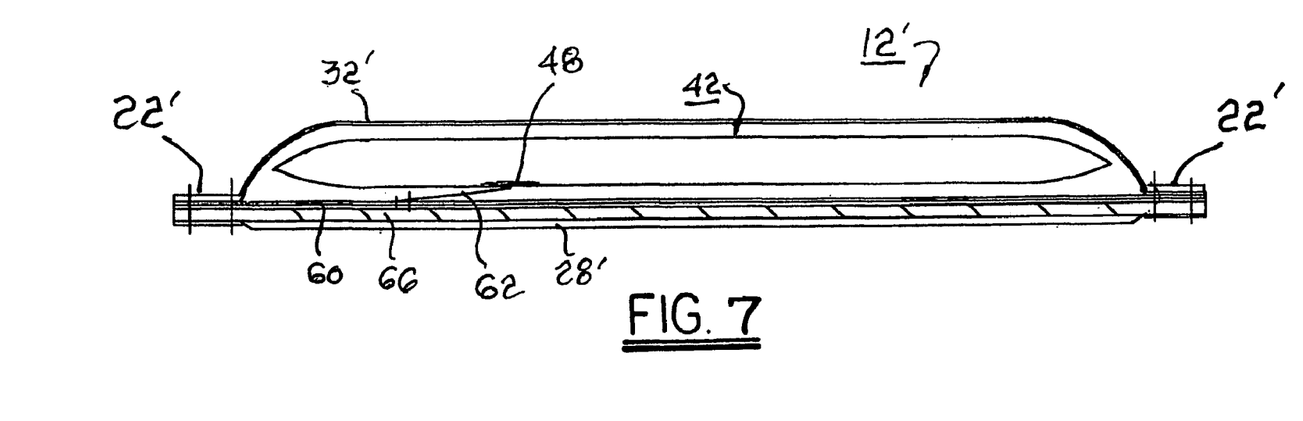
FIG. 7 is a cross-sectional view taken along line 7—7 in FIG. 5.

A second distinct difference and improvement upon the prior art is the inclusion between layers 28',32' of a discrete pneumatic bladder 42 comprising an inner wall 44 and an outer wall 46 defining therebetween a pneumatic chamber 34'. As in the prior art, chamber 34' is connectable to the actuation and control portion of the machine via one or more air hoses 36. Bladder 42 is preferably formed of a single piece of highly flexible, non-distensible, sheet material, preferably heat-sealed or ultrasonically-sealed, along a longitudinal seam 48 and across the longitudinal ends 50 to form a closed envelope. The transverse (cuff contact width) dimension of bladder 42 is selected such that bladder 42 is not included in longitudinal stitching 22', as shown in FIG. 7. Ends 50, however, are included in stitching 24', as shown in FIG. 6. Therefore, upon inflation, bladder 42 is longitudinally constrained by stitching 20' but is not constrained transversely, which is a third distinct difference and improvement upon the prior art.

Cuff sub-assembly 52 is well-suited for use as a closed cuff 12 in either an automatic blood pressure measurement machine or a stand-alone use. Referring to FIGS. 4 and 5, sub-assembly 52 is conveniently rolled into a generally cylindrical form, and sealed ends 50 and stitchings 24 may be joined 54 as by adhesive or further stitching.

Figure 8:
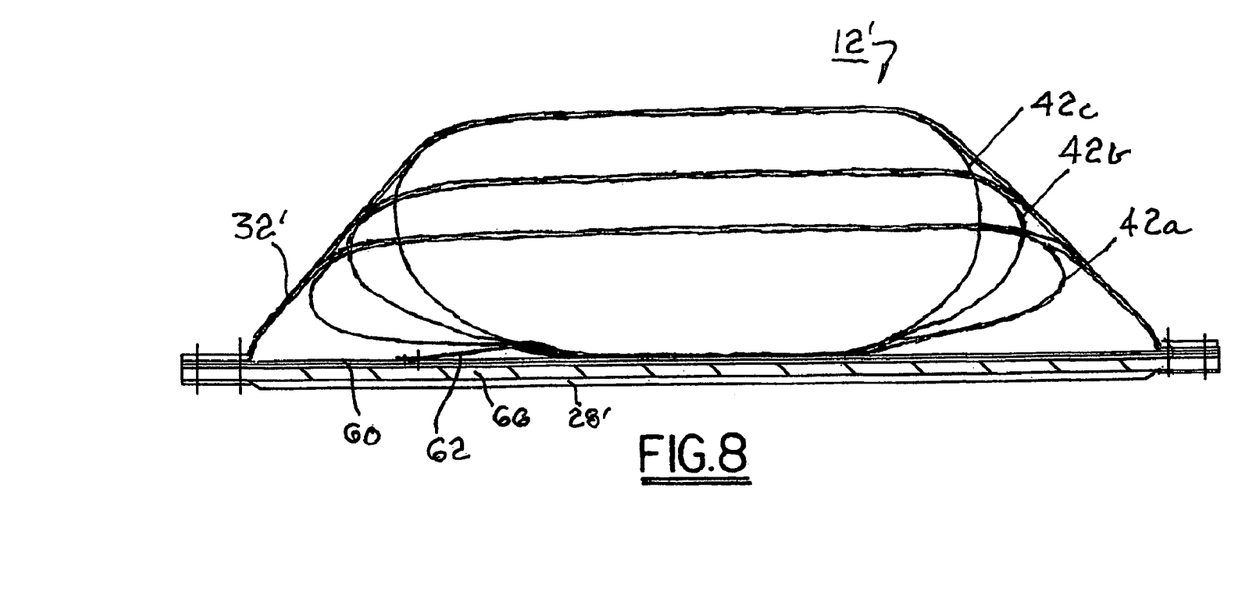
FIG. 8 is a cross-sectional view like that shown in FIG. 7, showing progressive inflation of a cuff bladder in accordance with the invention.
Figure 9:
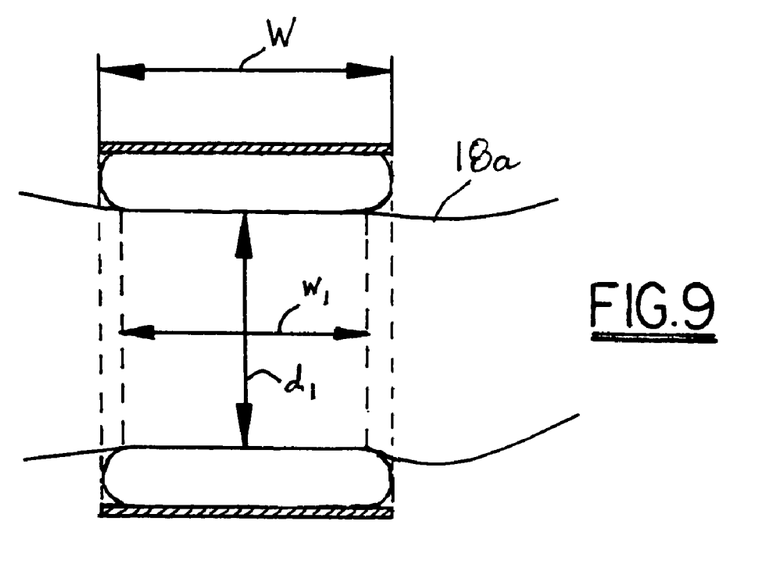
FIG. 9 is a schematic cross-sectional view showing an improved closed cuff in use on a large-diameter arm.
Figure 10:
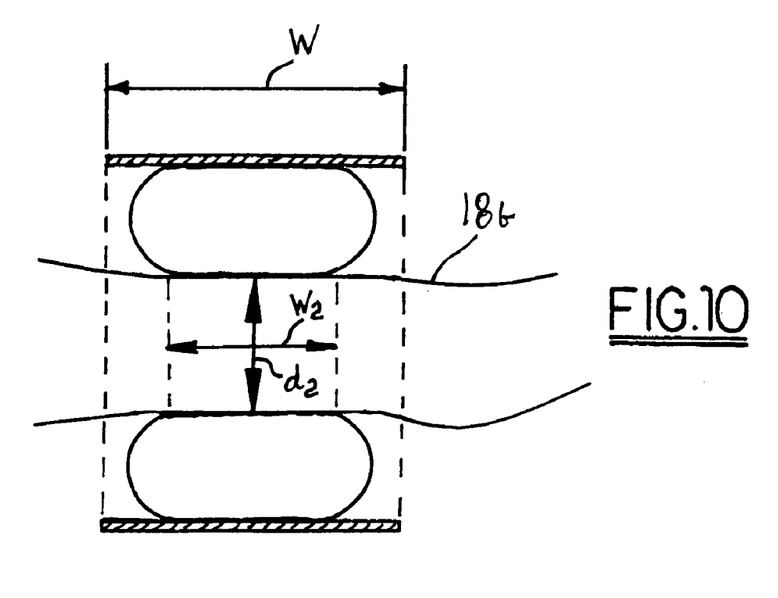
FIG. 10 is a schematic cross-sectional view showing an improved closed cuff in use on a small-diameter arm.

The benefit of not having the longitudinal edges of the pneumatic chamber constrained, as they are in the prior art, is shown in FIGS. 8 through 10. FIG. 8 shows bladder 42 in three different degrees of inflation, corresponding to use in three different sizes of arms. For an arm having a large diameter and circumference, the bladder assumes a relatively flat oval 42a in cross-sectional shape, having a relatively long cuff-width extent which is desirable for a large-diameter arm. For arms having progressively smaller diameters and circumferences, the bladder assumes a progressively less-flat oval 42b,42c having a progressively shorter cuff-width extent. Recall that the desired cuff contact width is about 40% of the cuff contact length. When the cuff 12' is sized for that relationship for the largest circumference (diameter may be used interchangeably for circumference in this discussion, since the relationship is fixed geometrically), the cuff is able to automatically assume a shorter cuff contact width as the arm diameter decreases, thus maintaining the desired relationship over a much wider range of arm sizes than is possible with a prior art cuff having all edges of the pneumatic chamber constrained.

This benefit is further illustrated in FIGS. 9 and 10. The width W of outer layer 28' remains constant, but the cuff width w of bladder 42 decreases as the diameter d of the subject arm 18 decreases. In this comparison, $w_1/d_1$ for arm 18a is about the same as $w_2/d_2$ for arm 18b. Thus, blood pressure measurements on the two arms are comparable for accuracy.

An additional and serendipitous benefit of a cuff in accordance with the invention is that a measurement bias caused by stretch resistance of the inner layer is offset by an opposite measurement bias caused by non-linear change in cuff contact length as a function of arm size. Thus, net linearity of results is extended over an even greater range of arm sizes than originally expected, for example, arm circumferences between about 18 cm and about 50 cm.

Referring again to FIGS. 4, 6, and 7, in a currently preferred embodiment, some additional elements may be optionally included to improve stability and performance of cuff 12'. A relatively thick, non-distensible backing layer 66 may be provided between bladder 42 and outer layer 28' to maintain structural shape and integrity of cuff 12' when deflated and to prevent the cuff from being inadvertently dragged out of housing 12. Preferably, layer 66 is formed of a rollable, heavy gauge, plastic sheeting. An outer fabric slip layer 60 may be inserted between bladder 42 and backing layer 66. Preferably, a longitudinal fin 62 on the back side of bladder 42 is formed when forming overlap seal 48. Fin 62 is stitched 64 to layer 60 and or backing layer 66 to prevent displacement of the bladder when an arm is being inserted into or removed from the cuff.

Referring again to FIG. 8, elastic inner layer 32' stretches as needed to accommodate all sizes and shapes to which bladder 42 may be inflated. Being elastic, layer 32' further assists in deflating bladder 42 during the deflation portion of its use cycle. The action of removing an arm, or entering a succeeding arm into the funnel-like cuff entrance formed by layer 32', assists in deflating bladder 42.

Figure 11:
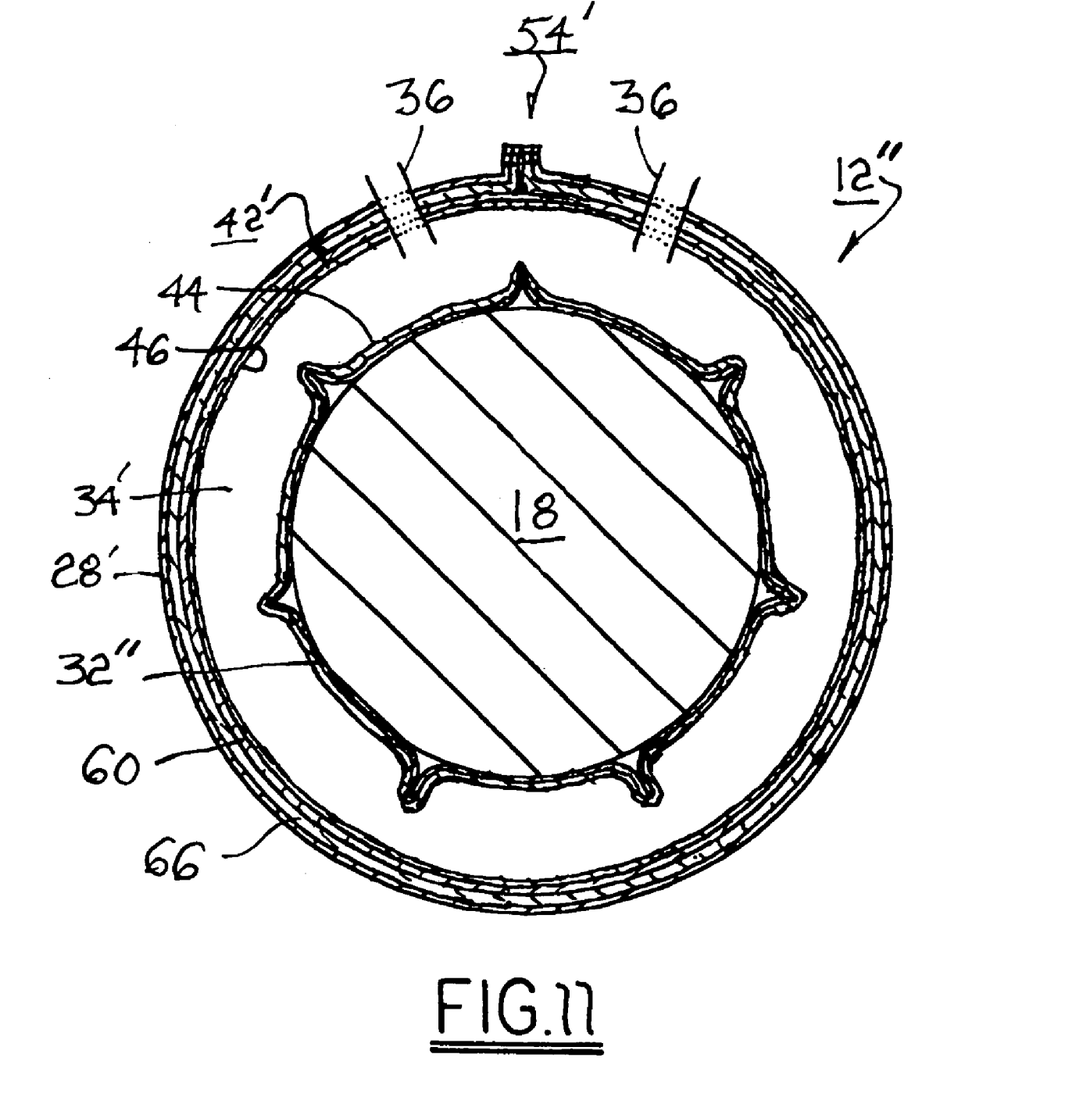
FIG. 11 is a cross-sectional view of a second embodiment of an improved closed cuff in accordance with the invention

Referring to FIG. 11, a second embodiment 12" of a closed cuff in accordance with the invention includes a bladder 42' formed as a continuous ring-shaped element similar to an inner tube for an automotive tire. Inner layer 32" is formed as a cylindrical sleeve. Because this configuration lacks sealed bladder ends as in first bladder embodiment 42, the cylindrical closure and seal 54' includes only the layers 28',66, et al. outboard of bladder 42'.

While the invention has been described by reference to various specific embodiments, it should be understood that numerous changes may be made within the spirit and scope of the inventive concepts described. Accordingly, it is intended that the invention not be limited to the described embodiments, but will have full scope defined by the language of the following claims.

What is claimed is:

1. A cuff for use in inferential measurement of animal systolic and/or mean and/or diastolic blood pressures, comprising:
   a) an elongate outer layer of material;
   b) an elongate inner layer of material attached to said outer layer of material along adjacent edges thereof; and
   c) an inflatable elongate bladder disposed between said inner and outer material layers, said bladder having first and second elongate ends and first and second lateral edges, wherein said bladder is attached to said inner and outer layers along said first and second elongate bladder ends, and is free of said inner and outer layers along said first and second lateral bladder edges.

2. A cuff in accordance with claim 1 wherein said first and second elongate ends of said outer and inner material layers are permanently connected such that said cuff defines a permanent tubular shape wherein said outer layer defines an outer surface thereof and said inner layer defines an inner surface thereof.

3. A cuff in accordance with claim 1 wherein said material forming said inner layer is dimensionally elastic and said material forming said outer layer is dimensionally inelastic.

4. A cuff in accordance with claim 3 wherein said inner layer material is provided with means for inhibiting permeation of water through said material.

5. A cuff in accordance with claim 1 wherein said bladder is attached to an outer layer of said cuff between said first and second elongate bladder ends.

6. A cuff in accordance with claim 1 further comprising a second relatively stiff intermediate layer disposed between said bladder and said outer layer for providing structural support for said cuff.

7. A cuff in accordance with claim 6 wherein said second layer is formed of rollable plastic sheeting.

8. A cuff in accordance with claim 1 wherein said outer layer material is selected from the group consisting of nylon shell and rollable plastic sheeting.

9. A cuff in accordance with claim 1 further comprising means for connection of said bladder to a controllable source of pressurized air.

10. A cuff in accordance with claim 9 wherein said source is an automated blood pressure measurement machine.

11. A cuff in accordance with claim 2 wherein said cuff is suitable for incorporation into an automated blood pressure measurement machine.

12. A cuff in accordance with claim 2 wherein said cuff is suitable for stand-alone use.

13. A cuff in accordance with claim 2 wherein said cuff is suitable for use on subjects having arm circumferences between about 18 cm and about 50 cm.

14. An automated blood pressure measurement machine, comprising:

a) a cylindrical housing for receiving an inflatable cuff; and b) an inflatable cuff disposed in said housing, said cuff having an elongate outer layer of material, an elongate inner layer of material attached to said outer layer of material along adjacent edges thereof, and an inflatable elongate bladder disposed between said inner and outer material layers, said bladder having first and second elongate ends and first and second lateral edges, wherein said bladder is attached to said inner and outer layers along said first and second elongate bladder ends, and is free of said inner and outer layers along said first and second lateral bladder edges.

* * * * *